US00PP37606P2

(12) United States Plant Patent
Miyazaki

(10) Patent No.: US PP37,606 P2
(45) Date of Patent: Aug. 18, 2026

(54) ***PETUNIA* PLANT NAMED 'Surf 20511'**

(50) Latin Name: ***Petunia* x *hybrida***
Varietal Denomination: Surf 20511

(71) Applicant: Kiyoshi Miyazaki, Hikone (JP)

(72) Inventor: Kiyoshi Miyazaki, Hikone (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 19/397,987

(22) Filed: Nov. 23, 2025

(51) Int. Cl.
*A01H 5/02* (2018.01)
*A01H 6/82* (2018.01)

(52) U.S. Cl.
USPC ..... Plt./356.15
CPC ..... *A01H 6/824* (2018.05)

(58) Field of Classification Search
USPC ..... Plt./356.15
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Petunia* plant named 'Surf 20511', characterized by its upright to outwardly spreading plant habit; vigorous growth habit; freely branching habit; freely flowering habit; long flowering period; flowers that are white in color with light purple-colored throats and venation; and good garden performance.

2 Drawing Sheets

Figure 1:
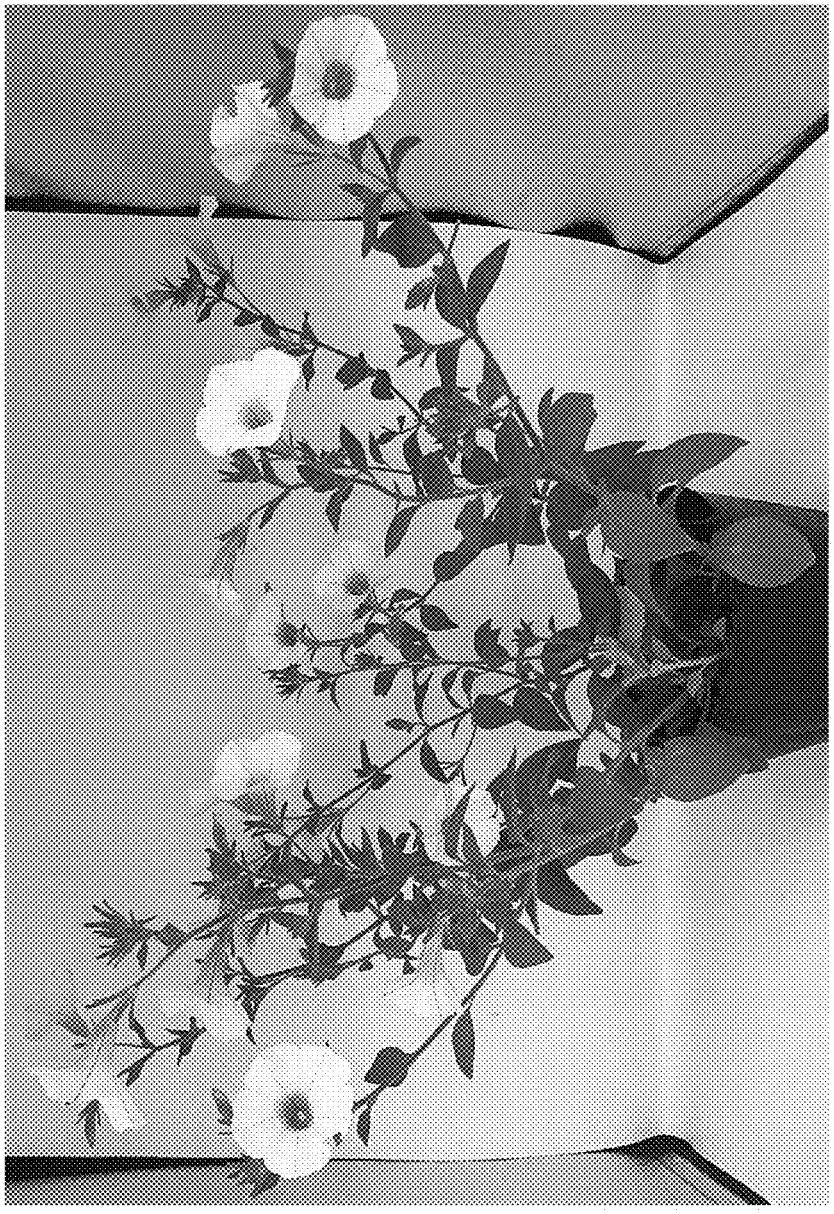

Botanical designation: *Petunia* x *hybrida*.
Cultivar denomination: 'Surf 20511'.

BACKGROUND OF THE INVENTION

The present invention relates to a new and distinct cultivar of Petunia plant, botanically known as *Petunia* x *hybrida* and hereinafter referred to by the name 'Surf 20511'.

The new *Petunia* plant is a product of a planned breeding program conducted by the Inventor in Higashiomi, Shiga, Japan. The objective of the breeding program is to create new outwardly spreading and freely-branching habit *Petunia* plants with numerous small white-colored flowers.

The new *Petunia* plant originated from a cross-pollination made by the Inventor in June, 2020 in Higashiomi, Shiga, Japan of a proprietary selection of *Petunia* x *hybrida* identified as code designation PV1835-1,not patented, as the female, or seed, parent with a proprietary selection of *Petunia* x *hybrida* identified as code designation PV1984-3, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in June, 2021.

Asexual reproduction of the new *Petunia* plant by terminal vegetative cuttings in a controlled greenhouse environment in Higashiomi, Shiga, Japan since April 2022 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Surf 20511'. These characteristics in combination distinguish 'Surf 20511' as a new and distinct *Petunia* plant:

1. Upright to outwardly spreading plant habit.
2. Vigorous growth habit.
3. Freely branching habit.
4. Freely flowering habit.
5. Long flowering period.
6. Flowers that are white in color with light purple-colored throats and venation.
7. Good garden performance.

Plants of the new *Petunia* can be compared to plants of the female parent selection. Plants of the new *Petunia* differ primarily from plants of the female parent selection in flower color as flowers of plants of the new *Petunia* are white in color with light purple-colored throats and venation whereas flowers of plants of the female parent selection are purple in color. In addition, plants of the new *Petunia* have smaller flowers than plants of the female parent selection.

Plants of the new *Petunia* can be compared to plants of the male parent selection. Plants of the new *Petunia* differ primarily from plants of the male parent selection in flower color as flowers of plants of the new *Petunia* are white in color with light purple-colored throats and venation whereas flowers of plants of the male parent selection are solid white in color. In addition, plants of the new *Petunia* have smaller flowers than plants of the male parent selection.

Plants of the new *Petunia* can also be compared to plants of the *Petunia* x *hybrida* 'Sunsurfsirou', disclosed in U.S. Plant Pat. No. 24,453. In side-by-side comparisons, plants of the new *Petunia* and 'Sunsurfsirou' differ primarily in the following characteristics:

1. Plants of the new *Petunia* are more upright than and not as spreading and mounding as plants of 'Sunsurfsirou'.
2. Plants of the new *Petunia* are more freely flowering than plants of 'Sunsurfsirou'.

3. Plants of the new *Petunia* have smaller flowers than plants of 'Sunsurfsirou'.

4. Plants of the new *Petunia* and 'Sunsurfsirou' differ in flower venation color as flowers of plants of the new *Petunia* have light purple-colored venation whereas flowers of plants of 'Sunsurfsirou' have light yellowish green-colored venation.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'Surf 20511' grown in a container.

Figure 2:
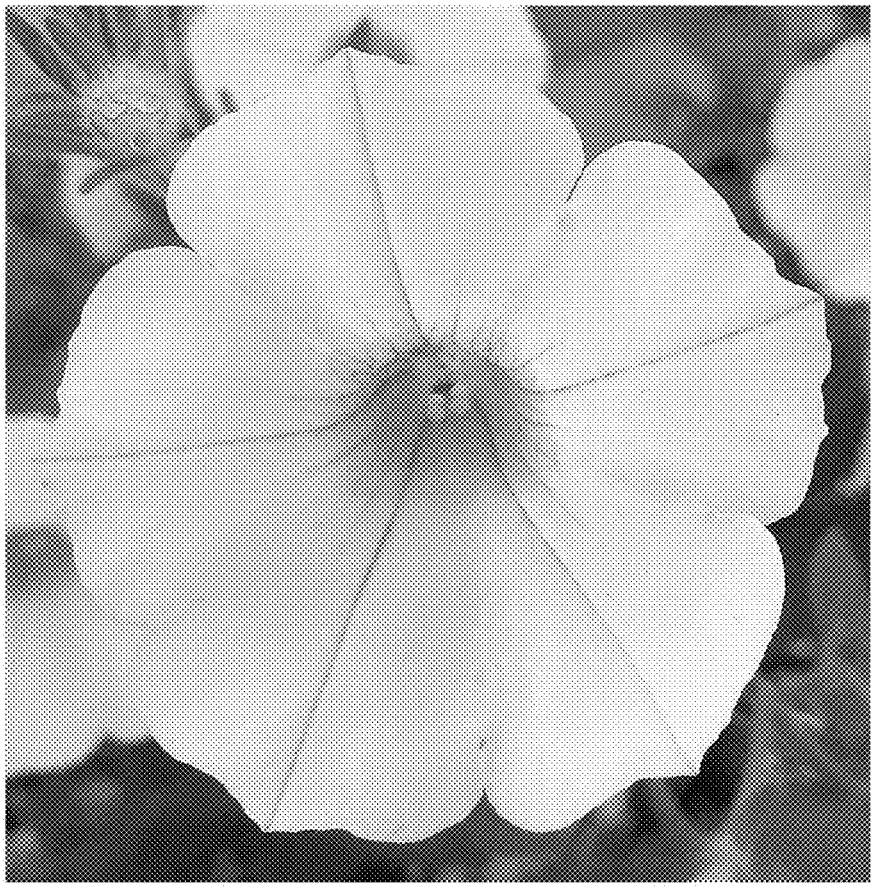

The photograph on the second sheet (FIG. 2) is a close-up view of a typical flower of 'Surf 20511'.

DETAILED BOTANICAL DESCRIPTION

The aforementioned photographs and following observations, measurements and values describe plants grown during the spring in 24-cm containers in an outdoor nursery in Higashiomi, Shiga, Japan and under cultural practices typical of commercial *Petunia* production. During the production of the plants, day temperatures averaged 23°° C. and night temperatures averaged 13°° C. Plants were six months old when the photographs and description were taken. In the following description, color references are made to The Royal Horticultural Society Colour Chart, 2015 Edition, except where general terms of ordinary dictionary significance are used.

Botanical classification:

*Petunia* x *hybrida* 'Surf 20511'.

Parentage:

*Female, or seed, parent.*—Proprietary selection of *Petunia* x *hybrida* identified as code designation PV1835-1, not patented.

*Male, or pollen, parent.*—Proprietary selection of *Petunia* x *hybrida* identified as code designation PV1984-3, not patented.

Propagation:

*Type.*—By terminal vegetative cuttings.

*Time to initiate roots, summer and winter.*—About one week at temperatures about 15°° C. to 20° C.

*Time to produce a rooted young plant, summer and winter.*—About three weeks at temperatures about 15°° C. to 20° C.

*Root description.*—Fibrous; typically white in color; actual color of the roots is dependent on substrate composition, water quality, fertilizer type and formulation, substrate temperature and physiological age of roots.

*Rooting habit.*—Freely branching; dense.

Plant description:

*Plant form and growth habit.*—Outwardly spreading plant habit; freely branching habit with numerous lateral branches developing per plant; pinching enhances lateral branch development; vigorous growth habit.

*Plant height.*—About 26.6 cm.

*Plant diameter.*—About 43.4 cm.

Lateral branch description:

*Length.*—About 28 cm.

*Diameter.*—About 2.3 mm.

*Internode length.*—About 2.6 cm.

*Strength.*—Strong, flexible.

*Aspect.*—Upright to outwardly.

*Texture.*—Pubescent; rough.

*Color.*—Close to 144B.

Leaf description:

*Quantity and arrangement.*—About 14 leaves per lateral branch; alternate, simple.

*Length.*—About 4.8 cm.

*Width.*—About 3.2 cm.

*Shape.*—Ovate.

*Apex.*—Obtuse.

*Base.*—Attenuate.

*Margin.*—Entire.

*Texture, upper and lower surfaces.*—Sparsely pubescent; rough.

*Venation pattern.*—Pinnate; reticulate.

Color.—*Developing and fully expanded leaves, upper surface: Close to* 144A; venation, close to 144C. Developing and fully expanded leaves, lower surface: Close to 144B; venation, close to 144C.

Petioles.—*Length:* About 6 mm. Diameter: About 2 mm. Texture, upper and lower surfaces: Pubescent; rough. Color, upper and lower surfaces: Close to 144A.

Flower description:

*Flower arrangement and habit.*—Single-type salverform flowers arising from upper leaf axils; freely flowering habit with usually about five flowers developing per lateral branch and about 32 flower buds and flowers developing per plant; flowers face upright to outwardly.

*Fragrance.*—None detected.

*Natural flowering season.*—Early flowering habit; plants of the new Petunia initiate and develop flowers about seven weeks after planting; long flowering period, flowering commences naturally during the spring and plants flower continuously throughout the summer and into the late autumn in Japan.

*Flower longevity.*—Individual flowers last about seven to ten days on the plant; flowers not persistent.

Flower buds.—*Length:* About 3.1 cm. Diameter: About 5 mm. Shape: Cylindrical. Color: Immature sepals, close to 145C; immature petals, close to 158C with venation, close to 145B.

*Flower diameter.*—About 3.9 cm.

*Flower tube length.*—About 2.2 cm.

*Flower tube diameter, distally.*—About 9.4 mm.

*Flower tube diameter, proximally.*—About 2.3 mm.

Corolla.—*Quantity and arrangement: Five petals in a single whorl, fused at the base and opening into a flared trumpet. Petal length from throat: About* 1.6 cm. Petal width: About 1.9 cm. Petal shape: Roughly spatulate. Petal apex: Cuspidate. Petal margin: Entire; slightly undulate. Petal texture, upper and lower surfaces: Smooth, glabrous. Throat texture: Smooth, glabrous. Tube texture: Pubescent; rough. Color: Petal lobe, when opening, upper and lower surfaces: Close to N155B; venation, close to N82D. Petal lobe, fully opened, upper surface: Close to N155A; venation, close to N82D; color does not change with subsequent development. Petal lobe, fully opened, lower surface: Close to NN155D; venation, close to N82D; color does not change with subsequent development. Throat: Distally and mid-section, close to 85D; proximally, close to 145D; venation, close to N82D. Tube: Distally and mid-section, close to 85D; proximally, close to 145D; venation, close to N82D.

*Calyx.*—Arrangement: One star-shaped calyx tube with five sepals arranged in a single whorl and fused at the base. Sepal length: About 1 cm. Sepal width: About 2.3 mm. Sepal shape: Linear. Sepal apex: Acute. Sepal margin: Entire. Sepal texture, upper and lower surfaces: Pubescent; rough. Color, upper surface: Close to 144A. Color, lower surface: Close to 144B.

Peduncles.—*Length: About* 1.8 cm. Diameter: About 1 mm. Strength: Moderately strong, flexible. Aspect: Upright to outwardly. Texture: Pubescent; rough. Color: Close to 144A.

*Reproductive organs.*—Stamens: Quantity per flower: Five. Filament length: About 1.5 cm. Filament color: Close to 150D. Anther shape: Ellipsoidal. Anther size: About 1.5 mm by 2 mm. Anther color: Close to 2D. Pollen amount: Sparse. Pollen color: Close to 2D. Pistils: Quantity per flower: One. Pistil length: About 1.8 cm. Style color: Close to 145C. Stigma shape: Transversely ellipsoidal. Stigma color: Close to 145A. Ovary color: Close to 145B Seeds and fruits: To date, seed and fruit development have not been observed on plants of the new *Petunia.*

Garden performance:

Plants of the new Petunia have been observed to have good garden performance and to tolerate rain, wind and temperatures ranging from about 5° C. to about 35° C.

Pathogen & pest resistance:

To date, plants of the new Petunia have not been observed to be resistant to pathogens and pests common to *Petunia* plants.

It is claimed:

1. A new and distinct *Petunia* plant named 'Surf 20511' as herein illustrated and described.

* * * * *